United States Patent
Harn et al.

(10) Patent No.: US 8,415,149 B2
(45) Date of Patent: Apr. 9, 2013

(54) HEPATIC PROGENITOR CELLS AND USES THEREOF

(75) Inventors: Horng-Jyh Harn, Taipei (TW); Shinn-Zong Lin, Taichung (TW)

(73) Assignee: Gwo Xi Stem Cell Applied Technology Co., Ltd., Zhubei, Hsinchu County (TW)

( * ) Notice: Subject to any disclaimer, the term of this patent is extended or adjusted under 35 U.S.C. 154(b) by 275 days.

(21) Appl. No.: 12/774,776

(22) Filed: May 6, 2010

(65) Prior Publication Data

US 2011/0274664 A1 Nov. 10, 2011

(51) Int. Cl.
*C12N 5/00* (2006.01)
*C12N 5/02* (2006.01)
*C12N 5/07* (2010.01)

(52) U.S. Cl. .................. 435/325; 435/363; 435/373

(58) Field of Classification Search .................. 435/325, 435/363, 370, 372; 424/583
See application file for complete search history.

(56) References Cited

U.S. PATENT DOCUMENTS

| 2007/0020242 A1* | 1/2007 | Ramiya ..................... 424/93.7 |
| 2007/0082397 A1 | 4/2007 | Hasson et al. |
| 2008/0071370 A1* | 3/2008 | Vinas ........................... 623/7 |
| 2009/0324607 A1 | 12/2009 | Reisner et al. |
| 2010/0087000 A1 | 4/2010 | McClelland |

OTHER PUBLICATIONS

Tsai et al., "The Therapeutic Potential of Human Umbilical Mesenchymal Stem Cells from Wharton's Jelly in the Treatment of Rat Liver Fibrosis," Liver Transplantation, 15:484-495 (2009).
Wang et al., "Mesenchymal Stem Cells in the Wharton's Jelly of the Human Umbilical Cord," Stem Cells, 22:1330-1337 (2004).

* cited by examiner

*Primary Examiner* — Ruth Davis
(74) *Attorney, Agent, or Firm* — Occhiuti Rohlicek & Tsao LLP

(57) ABSTRACT

Disclosed are cells, compositions, and methods for treating liver diseases.

11 Claims, 7 Drawing Sheets

US 8,415,149 B2

HEPATIC PROGENITOR CELLS AND USES THEREOF

BACKGROUND

Chronic liver diseases are a serious worldwide health problem. Hepatitis B, hepatitis C, alcohol and certain chemicals can result in liver fibrosis and cirrhosis, and ultimately in liver failure. Currently, liver transplantation remains the only curative option for patients with liver failure. However, its use is hampered by the lack of available donors. In addition, liver transplantation is not suitable for diseases, such as certain infections and types of cancer. There is a need for an alternative method for treating liver diseases and related conditions.

SUMMARY

This invention is based, at least in part, on unexpected discoveries that pluripotent, hepatic progenitor cells can be obtained and used to treat liver diseases and related conditions.

Accordingly, one aspect of this invention features a method for obtaining hepatic progenitor cells. The method includes obtaining a preparation containing cultured pluripotent animal cells that are (i) positive for one or more markers selected from group consisting of CD29, CD44, CD49b, CD49d, CD73, CD90, CD105, and CD13; and (ii) negative for one or more markers selected from group consisting of CD14, CD34, CD45, and HLA-DR; co-culturing the pluripotent animal cells with a co-culture liver tissue in a medium for a period of time; and collecting the co-cultured pluripotent animal cells or their progenies to obtain hepatic progenitor cells.

Preferably, the pluripotent animal cells are obtained from the Wharton's jelly of the umbilical cord of a first subject, which can be a human or a non-human mammal, such as a cat, a dog, a pig, or a horse. The co-culture liver tissue can be an injured liver tissue, which can be obtained by a process including subjecting a liver tissue from a second subject (which can also be a human or a non-human mammal) to a hepatotoxic agent, i.e., an agent that causes injury to liver. The first and second subject can be the same subject or different subjects. Examples of the hepatotoxic agent include a mechanical force, a physiological event (e.g., ischemia or inflammatory process), and a chemical agent, such as thioacetamide (TAA), $CCl_4$, or alcohol. The liver tissue can also be obtained, as a biopsy sample, from a subject that has been exposed to the hepatotoxic agent. The hepatic progenitor cells can express one or more of genes selected from the group consisting of CK18, albumin, tryptophan 2,3-dioxygenase (TO), αfetoprotein (AFP), CYP7A1, nanog, oct4, ckit, hepatocyte growth factor (HGF), and matrix metalloproteinase (MMP). In one example, the pluripotent animal cells are positive for HGF or MMP.

Another aspect of this invention features a preparation having the above-mentioned hepatic progenitor cells. The preparation can be prepared according to the method described above.

Another aspect of this invention features a composition having a preparation containing cultured pluripotent animal cells and a liver tissue. The pluripotent animal cells are (i) positive for one or more markers selected from group consisting of CD29, CD44, CD49b, CD49d, CD73, CD90, CD105, and CD13; and (ii) negative for one or more markers selected from group consisting of CD14, CD34, CD45, and HLA-DR;. The liver tissue can be an isolated/in vitro liver tissue. In one example, the liver tissue is an injured liver tissue that has been subjected to a hepatotoxic agent. The pluripotent animal cells can be obtained from the Wharton's jelly of the umbilical cord of a first subject, e.g., a human.

Another aspect of this invention features a method for treating a liver disease, such as, liver fibrosis or cirrhosis. The method includes identifying a subject having or at risk of having the disease, and administering to the subject an effective amount of (a) a first preparation containing the above-mentioned cultured pluripotent animal cells or (b) a second preparation containing the above-mentioned hepatic progenitor cells. The pluripotent animal cells or the hepatic progenitor cells, once administered to the subject, can differentiate into cells expressing albumin. The hepatic progenitor cells can be prepared according to the method described above.

Another aspect of this invention features a method for increasing the level of albumin, HGF, or metalloproteinase in the liver of a subject. The method includes administering to a subject in need thereof an effective amount of (a) a first preparation of the above-mentioned cultured pluripotent animal cells or (b) a second preparation of the above-mentioned hepatic progenitor cells. The hepatic progenitor cells can be prepared according to the method described above.

A hepatic progenitor cell refers to a cells (1) expressing one or more liver-specific genes, including CK18, albumin, TO, AFP, and CYP7A1; and (2) having the developmental potential to differentiate into hepatocytes. Hepatic progenitor cells have a decreased expression level of stem cell genes, including nanog, oct4, and ckit, as compared with the above-mentioned pluripotent animal cells obtained from the Wharton's jelly of the umbilical cord, i.e., Wharton's jelly stem cells (WJSC).

The details of one or more embodiments of the invention are set forth in the accompanying drawings and the description below. Other features, objects, and advantages of the invention will be apparent from the description and drawings, and from the claims.

DETAILED DESCRIPTION

Figure 1:
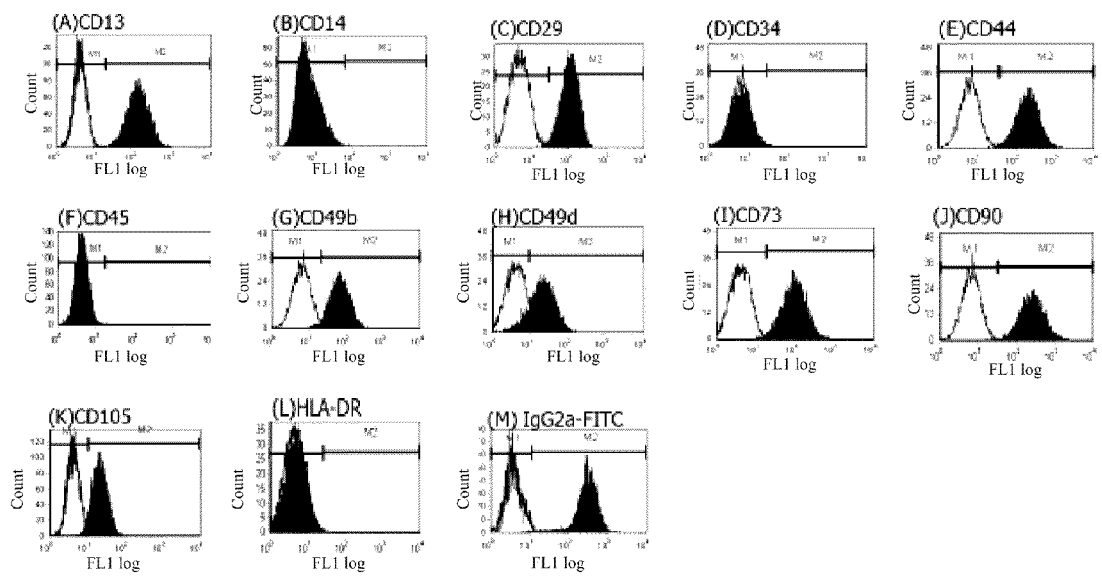
FIGS. 1A-N are diagrams of immunohistochemical staining with antibodies against CD13 (1A), CD14(1B), CD29 (1C), CD 34 (1D), CD44 (1E), CD45 (1F), CD49b (1G), CD49d (1H), CD73 (1I), CD90 (1J), CD105 (1K), HLA-DR (1L), and IgG2a-FITC (1M, as a positive control) and photographs (1N) showing surface phenotype (1A-1M) and typical morphology of WJSCs; in 1N, left panel: low-density culture; right panel: high-density culture. Bar=50 mm.
Figure 1:
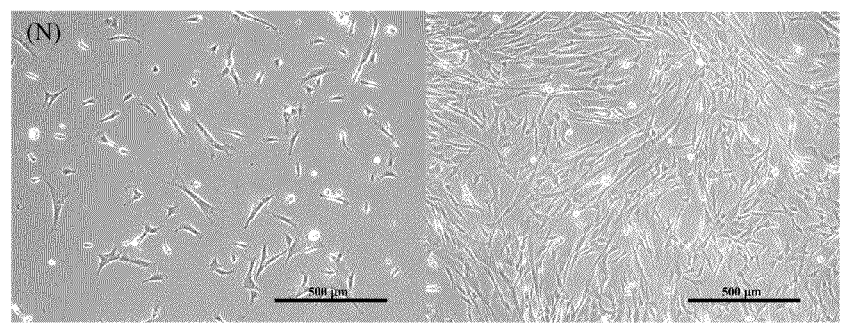

This invention relates to pluripotent cells and methods of using the cells in treating liver diseases.

Uses of stem cell therapy in the treatment of liver diseases have been suggested in medical research because of the self-renewal characteristics and differentiation potential of stem cells. Yet, ethical and logistical considerations have hampered the use of Embryonic stem (ES) cells. Stem cells derived from bone marrow or umbilical cord have the potential to become various kinds of cells and hepatic progenitor cells. In addition, in vivo studies indicate that transplanted stem cells can differentiate into hepatic progenitor cells and express specific markers such as albumin, tryptophan 2,3-dioxygenase and cytokeratin 18 (CK18). For example, transplantation of rat stem cells accelerates an animal's recovery following liver damage.

The present invention relates to using Wharton's jelly stem cells (WJSC) to obtain hepatic progenitor cells (HPC), which in turn can be used in treating liver diseases. Like ES cells, WJSCs possess potential to differentiate into various cells, including hepatic progenitor cells. They therefore can be used to regenerate liver cells for treating liver diseases. As shown in the example below, WJSCs can be easily isolated, maintained, and expanded in vitro, and induced to differentiate using routine technical approaches. In addition, after grafting WJSCs into mice, there is no evidence of mitotically active cells, teratomas, or malignant growth. These cells can be used for transplantation in treating liver diseases without the above-mentioned concerns. Due to these advantages, the cells represent an alternative to other pluripotent cells. In a preferred embodiment of this invention, human WJSCs (HWJSCs) are used.

Wharton's jelly is a gelatinous connective tissue from the umbilical cord and composed of myofibroblast-like stromal cells, collagen fibers, and proteoglycans (Kobayashi et al., 1998, Early Hum Dev 51, 223-33). WJSCs can be easily isolated and expanded ex vivo. They have the developmental potential and, under suitable conditions, can differentiate into neuron-like cells, cartilage-like cells, and cells of adipogenic, cardiogenic, chondrogenic, or osteogenic lineage.

The cells from the Wharton's jelly of porcine umbilical cord could be cultured and maintained for more than 100 population doublings and continue to grow vigorously (Weiss, et al. 2003, Exp Neurol 182, 288-99). Immuno-histochemical and ultrastructual investigation reveals that cells from the Wharton's jelly possess characteristics of stromal cells, and show differentiated distribution pattern of various cytoskeletal and extracellular matrix proteins (Nanaev et al. 1997, Placenta 18, 53-64).

To prepare WJSCs, one can use the method described in the example 1 below. To confirm that the cells thus prepared are indeed WJSCs, specific surface molecules can be examined on, e.g., passage 4-8 generations of the above-described cells by, e.g., flow cytometric analysis or other standard immunochemical analysis. Antibodies against the antigens as mentioned above or in FIGS. 1A-1N can be used. The antibodies can be conjugated with suitable labels, such as fluorescein isothiocyanate (FITC), phycoerythrin (PE), or quantum dots. WJSCs, which are negative for CD14, CD 34, CD45, and HLA-DR, but positive for CD29, CD44, CD49b, CD49d, CD73, CD90, CD105, and CD13, can be further enriched or purified using flow cytometry.

The enriched WJSCs are then tested by standard techniques to confirm their differentiation potential. For example, fifth to tenth-passage cells can be induced to form HPCs, neuro-glial cells, osteocyte, and adipocyte by methods known in the art. To obtain HPCs, WJSCs can be cultured in the manner described in the example below. In another example, to confirm the osteogenic or adipogenic differentiation potential, WJSCs can be passed and cultured to confluence, shifted to an osteogenic medium or an adipogenic medium, and incubated for suitable time (e.g., 3 weeks). The differentiation potential for osteogenesis can be assessed by mineralization of calcium accumulation, which can be visualized by von Kossa staining. To examine adipogenic differentiation, intracellular lipid droplets can be stained by Oil Red O and observed under a microscope. For neural differentiation, WJSCs can be incubated in a neurogenic medium for suitable duration (e.g., 7 days), and then subjected to serum depletion and incubation of β-mercaptoethanol. After differentiation, WJSCs exhibit the morphology of refractile cell body with extended neuritelike structures arranged into a network. Immunocytochemical stain of lineage specific markers can be further conducted to confirm neural differentiation. Examples of the markers include neuron specific class III β-tubulin (Tuj-1), neurofilament, and GFAP.

The above-described WJSCs or HPCs can be propagated in a non-differentiating medium culture for many population doublings without indications of spontaneous differentiation, senescence, morphological changes, increased growth rate, or changes in ability to differentiate into liver cells.

The WJSCs or HPCs thus confirmed can be stored by standard methods or can be administered to a subject in need thereof as described below.

The present invention can be practiced with various totipotent or pluripotent stem cells that can differentiate into HPCs. In other words, the stem and/or progenitor cells used in the present invention can be of various origins in addition to WJSCs. In one embodiment, the stem and/or progenitor cells are derived from a source selected from the group consisting of hematopoietic cells, umbilical cord blood cells, G-CSF mobilized peripheral blood cells, bone marrow cells, hepatic cells, pancreatic cells, neural cells, oligodendrocyte cells, skin cells, embryonal stem cells, muscle cells, bone cells, mesenchymal cells, chondrocytes and stroma cells. Methods of preparation of stem cells from a variety of sources are well known in the art, commonly selecting cells expressing one or more stem cell markers such as CD34, CD133, etc, or lacking markers of differentiated cells. Selection is usually by FACS, or immunomagnetic separation, but can also be by nucleic acid methods such as PCR-based methods. ES cells and methods of their retrieval are well known in the art and are described in, e.g., Smith, Annu Rev Cell Dev Biol (2001) 17:435. Adult stem cells, i.e., stem cells derived from tissues of adults, are also well known in the art. Methods of isolating or enriching for adult stem cells are described in, for example, Miraglia et al. (1997) Blood 90: 5013, Uchida et al. (2000) Proc. Natl. Acad. Sci. USA 97: 14720, Simmons, P. J. et al. (1991) Blood 78: 55, Prockop Cytotherapy (2001) 3: 393, Bohmer Fetal Diagn Ther (2002) 17: 83; and Rowley et al. Bone Marrow Transplant (1998) 21: 1253), Stem Cell Biology Daniel R. Marshak (Editor) Richard L. Gardner (Editor), Publisher: Cold Spring Harbor Laboratory Press, (2001) and Hematopoietic Stem Cell Transplantation. Anthony D. Ho (Editor) Richard Champlin (Editor), Publisher: Marcel Dekker (2000).

The term "stem cell" refers to a cell that is capable of differentiating into a number of final, differentiated cell types. Stem cells may be totipotent or pluripotent. Totipotent stem cells typically have the capacity to develop into any cell type. Totipotent stem cells can be both embryonic and non-embryonic in origin. Pluripotent cells are typically cells capable of differentiating into several different, final differentiated cell types. Unipotent stem cells can produce only one cell type, but have the property of self-renewal which distinguishes them from non-stem cells. These stem cells can originate from various tissue or organ systems, including, but not limited to, blood, nerve, muscle, skin, gut, bone, kidney, liver, pancreas, thymus, and the like. In accordance with the present invention, the stem cell can be derived from an adult or neonatal tissue or organ.

The cells described in this invention are substantially pure. The term "substantially pure", when used in reference to stem cells or cells derived therefrom (e.g., differentiated cells), means that the specified cells constitute a substantial portion of or the majority of cells in the preparation (i.e., more than 20%, 30%, 40%, 50%, 60%, 70%, 80%, 90%, or 95%). Generally, a substantially purified population of cells constitutes at least about 70% of the cells in a preparation, usually about 80% of the cells in a preparation, and particularly at least about 90% of the cells in a preparation (e.g., 95%, 97%, 99% or 100%). In other words, a population of heterogeneous or homogenous cells can be used in this invention.

The terms "proliferation" and "expansion" as used interchangeably herein with reference to cells, refer to an increase in the number of cells of the same type by division. The term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. Differentiation may be assessed, for example, by monitoring the presence or absence of lineage markers, using immunohistochemistry or other procedures known to a worker skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages. The terms "lineage commitment" and "specification," as used interchangeably herein, refer to the process a stem cell undergoes in which the stem cell gives rise to a progenitor cell committed to forming a particular limited range of differentiated cell types. Committed progenitor cells are often capable of self-renewal or cell division. The term "terminal differentiation" refers to the final differentiation of a cell into a mature, fully differentiated cell. For example, hematopoietic progenitor cells and muscle progenitor cells can differentiate into neural or glial cell lineages, terminal differentiation of which leads to mature neurons or glial cells. Usually, terminal differentiation is associated withdrawal from the cell cycle and cessation of proliferation. The term "progenitor cell," as used herein, refers to a cell that is committed to a particular cell lineage and which gives rise to cells of this lineage by a series of cell divisions.

The present invention provides for pharmaceutical compositions containing the above-descried cells or active agents/compounds. Pharmaceutical compositions can be prepared by mixing a therapeutically effective amount of the cells or active agents/compounds, and, optionally other active substance, with a pharmaceutically acceptable carrier. The carrier can have different forms, depending on the route of administration.

The above-described pharmaceutical compositions can be prepared by using conventional pharmaceutical excipients and methods of preparation. All excipients may be mixed with disintegrating agents, solvents, granulating agents, moisturizers, and binders. As used herein, the term "effective amount" or 'therapeutically effective amount' refers to an amount which results in measurable amelioration of at least one symptom or parameter of a specific disorder. A therapeutically effective amount of the above-descried cells can be determined by methods known in the art. An effective amount for treating a disorder can easily be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician.

The phrase "pharmaceutically acceptable" refers to molecular entities and other ingredients of such compositions that are physiologically tolerable and do not typically produce unwanted reactions when administered to a human. Preferably, the term "pharmaceutically acceptable" means approved by a regulatory agency of the federal or a state government or listed in the U.S. Pharmacopeia or other generally recognized pharmacopeia for use in mammals, and more particularly in humans. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

A carrier applied to the pharmaceutical compositions described above refers to a diluent, excipient, or vehicle with which a compound is administered. Such pharmaceutical carriers can be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The above-descried cells can be administered to individuals through infusion or injection (for example, intravenous, intrathecal, intramuscular, intraluminal, intratracheal, intraperitoneal, or subcutaneous), orally, transdermally, or other methods known in the art. Administration may be once every two weeks, once a week, or more often, but frequency may be decreased during a maintenance phase of the disease or disorder.

Both heterologous and autologous cells can be used. In the former case, HLA-matching should be conducted to avoid or minimize host reactions. In the latter case, autologous cells are enriched and purified from a subject and stored for later use. The cells may be cultured in the presence of host or graft T cells ex vivo and re-introduced into the host. This may have the advantage of the host recognizing the cells as self and better providing reduction in T cell activity.

The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the above-described composition. Dosages and administration regimen can be adjusted depending on the age, sex, physical condition of administered as well as the benefit of the conjugate and side effects in the patient or mammalian subject to be treated and the judgment of the physician, as is appreciated by those skilled in the art. In all of the above-described methods, the cells can be administered to a subject at $1\times10^4$ to $1\times10^{10}$/time.

Within the scope of this invention is a method of treating a liver disorder or alleviate the symptom of the disorder in a subject. The method includes identifying a subject in need thereof (e.g., suffering from or being at risk for developing a liver disorder) and administering or implanting the cells described herein.

Administering/implanting can be carried out by direct injection into a target organ, injection into the bloodstream, intraperitoneal injection, etc. Suitable methods of administration/implantation can be determined by monitoring the homing of the implanted cells to the desired organ, the expression of desired organ-specific genes or markers, and the function of the organ of the subject, such as albumin or HGF synthesis. It will be appreciated that ex-vivo expanded stem and/or progenitor cells can be implanted into liver in order to provide the cells with an environment conducive to differentiation into cells expressing characters specific to cells of the liver, and that cells thus differentiated can be removed, reisolated, and further reimplanted into other parts of the liver or other subjects.

The subject can be a human or a non-human mammal, such as a cat, a dog, a pig, or a horse. Examples of the liver disorder include liver fibrosis and cirrhosis. The phrase "in need thereof" indicates the state of the subject, wherein enhancement of liver is desirable. Such a state can include, but is not limited to, subjects suffering from primary liver disease such as primary biliary cirrhosis, hepatic cancer, primary sclerosing cholangitis, autoimmune chronic hepatitis, alcoholic liver disease and infectious disease such as hepatitis C, secondary conditions such as the hepatic stage of parasitic infections (helminthes, etc), drug and chemical toxicity. In any of the methods of this aspect of the present invention, the donor and the recipient of the stem and/or progenitor cells can be a single individual or different individuals, for example, allogeneic or xenogeneic individuals. When allogeneic transplantation is practiced, regimes for reducing implant rejection and/or graft vs. host disease, as well know in the art, should be undertaken. Such regimes are currently practiced in human therapy. See, e.g., Slavin et al., e.g., J Clin Immunol (2002) 22: 64, and J. Hemather Stem Cell Res (2002) 11: 265), Gur et al. (Blood (2002) 99: 4174), and Martelli et al, (Semin Hematol (2002) 39: 48), which are incorporated herein by reference.

A subject to be treated can be identified by standard techniques for diagnosing the conditions or disorders of interest. For example, excess deposition of collagen is the main characteristic of liver fibrosis induced by chronic viral hepatitis, alcohol abuse and drug toxicity.

The treatment method entails administering to a subject in need thereof an effective amount of the above-described cells. The therapeutic effects of the above-described cells can be accessed according to standard methods (e.g., those described in the example below).

Also within the scope of this invention is a method of increasing the level of albumin, HGF, metalloproteinase (e.g., MMP) in the liver of a subject. The method includes administering to a subject in need thereof an effective amount of (a) a first preparation of cultured pluripotent animal cells or (b) a second preparation of hepatic progenitor cells. The pluripotent animal cells are (i) positive for one or more markers selected from group consisting of CD29, CD44, CD49b, CD49d, CD73, CD90, CD105, and CD13; and (ii) negative for one or more markers selected from group consisting of CD14, CD34, CD45, and HLA-DR. Metalloproteinase plays an important role in digesting collagen in cirrhosis of liver, and studies have revealed that increased expression of metalloproteinase can help to degrade collagen in the cirrhosis of liver.

One can measure the expression level of albumin, HGF, or metalloproteinase in a sample obtained from the subject before or after administration to confirm efficacy. The expression level can be determined at either the mRNA level or the protein level. Methods of measuring mRNA levels in a tissue sample or a body fluid are well known in the art. To measure mRNA levels, cells can be lysed and the levels of mRNA in the lysates, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNA protection assay (RPA) method and the serial analysis of gene expression (SAGE) method, as well as array-based technologies.

Methods of measuring protein levels in a tissue sample or a body fluid are well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Some protein-measuring assays (e.g., ELISA or Western blot) can be applied to body fluids or to lysates of cells, and others (e.g., immunohistological methods or fluorescence flow cytometry) can be applied to histological sections or unlysed cell suspensions. Appropriate labels include radionuclides (e.g., $^{125}$I, $^{131}$I, $^{35}$S, $^3$H, or $^{32}$P), enzymes (e.g., alkaline phosphatase, horseradish peroxidase, luciferase, or β-glactosidase), fluorescent/luminescent agents (e.g., fluorescein, rhodamine, phycoerythrin, GFP, BFP, and Qdot™ nanoparticles supplied by the Quantum Dot Corporation, Palo Alto, Calif.). Other applicable methods include quantitative immunoprecipitation or complement fixation assays.

Based on the results from the assays described above, an appropriate dosage range and administration route can be determined. The dosage required depends on the choice of the route of administration; the nature of the formulation; the nature of the patient's illness; the subject's size, weight, surface area, age, and sex; other drugs being administered; and the judgment of the attending physician. Dosage variations are necessary in view of the different efficiencies of various routes of administration. The variations can be adjusted using standard empirical routines for optimization as is well understood in the art. In general, $1 \times 10^4$ and $1 \times 10^7$ (e.g., $1 \times 10^5$ to $5 \times 10^6$ and more preferably $5 \times 10^5$ to $2 \times 10^5$) cells are administered. Multiple sites can be used depending on the site and nature of particular treatment. As mentioned above, both heterologous and autologous WJSCs or HPCs can be used. In the former case, HLA-matching should be conducted to avoid or minimize host reactions. In the latter case, autologous cells are enriched and purified from a subject and stored for later use.

"Treating" refers to administration of a composition (e.g., a cell composition) to a subject, who is suffering from or is at risk for developing a liver disease or a disorder causing such a disease, with the purpose to cure, alleviate, relieve, remedy, or ameliorate the damage/disorder, the symptom of the damage/disorder, the disease state secondary to the damage/disorder, or the predisposition toward the damage/disorder. Examples of liver disease include primary liver disease such as primary biliary cirrhosis, hepatic cancer, primary sclerosing cholangitis, autoimmune chronic hepatitis, alcoholic liver disease (the most common cause of liver injury) and infectious disease (such as hepatitis A, B, or C), as well as secondary conditions such as the hepatic stage of parasitic infections (helminthes, etc), drug and chemical toxicity, many of which are life threatening. Furthermore, due to the liver's critical roles in metabolism and homeostasis, such as albumin synthesis, and unique vascularization, impaired liver function has serious consequences for the nervous, skeletal, digestive, endocrine and circulatory systems.

An "effective amount" refers to an amount of the composition that is capable of producing a medically desirable result in a treated subject. The treatment method can be performed alone or in conjunction with other drugs or therapies.

In one embodiment, the above-described cells and methods can be used to facilitate the efficient establishment of ex-vivo expanded populations of stem and/or progenitor cells derived from cord blood, bone marrow, peripheral blood or endodermal organ cells suitable for transplantation into liver. Specifically, the ex-vivo expanded cells can be used to treat diseases of, and restore function in liver. The methods of the invention can also be used for applications in cellular gene therapy of transplanted, repopulated organs.

The above-described methods may further include administering the subject with a minimal immunosuppressive regimen prior to, concomitantly with, or following transplantation of the cells. Various types of immunosuppressive regimens may be used. Examples include administration of immunosuppressive drugs, tolerance inducing cell populations, and/or immunosuppressive irradiation. Guidance for selecting and administering suitable immunosuppressive regimens for transplantation is well known in the art (e.g., Kirkpatrick et al., 1992. JAMA. 268, 2952; Higgins et al., 1996. Lancet 348, 1208; Suthanthiran et al., 1996. New Engl. J. Med. 331, 365; Midthun et al., 1997. Mayo Clin Proc. 72, 175; Morrison et al., 1994. Am J. Med. 97, 14; Hanto 1995 Annu Rev Med. 46, 381; Senderowicz et al., 1997. Ann Intern Med. 126, 882; Vincenti et al., 1998. New Engl. J. Med. 338, 161; Dantal et al. 1998. Lancet 351, 623).

Examples of suitable immunosuppressive drugs include CTLA4-Ig, anti-CD40 antibodies, anti-CD40 ligand antibodies, anti-B7 antibodies, anti-CD3 antibodies (for example, anti-human CD3 antibody OKT3), methotrexate (MTX), prednisone, methyl prednisolone, azathioprene, cyclosporin A (CsA), tacrolimus, cyclophosphamide and fludarabin, mycophenolate mofetil, daclizumab (a humanized (IgG1 Fc) anti-IL2R alpha chain (CD25) antibody), anti-T-lymphocyte antibodies conjugated to toxins (for example, cholera A chain, or Pseudomonas toxin), and an agent capable of inhibiting the activity of the protein mammalian-target-of-rapamycin (mTOR).

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE

Experimental Procedures
Culture of WJSCs

The WJSCs used in this study were isolated from a donated human umbilical cord with the donor's consent, according to a previously reported protocol (Wang et al., 2004, Stem Cells 22(7):1330-1337). The WJSCs isolation was approved by the Institutional Review Board of Buddhist Tzu Chi General Hospital. The cells obtained were cultured and expanded in Iscove's Modified Dulbecco's Medium (IMDM; INVITROGEN, Carlsbad, Calif., USA) supplemented with 10% fetal bovine serum (HYCLONE, Logan, Utah, USA), 10 ng/mL basic fibroblast growth factor (R&D, Minneapolis, Minn., USA), 2 mM L-glutamine and 100 U/L penicillin-streptomycin (INVITROGEN, Carlsbad, Calif., USA) in a 37° C. incubator with 5% $CO_2$. Cells with passage numbers 10 to 20 were used in this study.

Characterization of WJSCs

WJSC surface markers were analyzed by flow cytometry (FC500; BECKMAN COULTER, Brea, Calif., USA) after being labeled with various antibodies, including those against human CD105 (SANTA CRUZ BIOTECHNOLOGY, Santa Cruz, Calif., USA); CD13, CD14, CD29, CD34, CD44, CD45, HLA-DR and IgG2a (DAKO, Carpinteria, Calif., USA) and CD49b, CD49d, CD73 and CD90 (BECTON DICKINSON, Franklin Lakes, N.J., USA). Secondary antibodies conjugated with fluorescein isothiocyanate (CHEMICON, Temecula, Calif., USA) were used for detection.

In Vitro Hepatic Differentiation

In vitro hepatic differentiation was carried out by a modified co-culture protocol as described by Jang et al., 2004, Nat. Cell Biol. 6(6):532-539. Briefly, Wyss ($3 \times 10^4$) were co-cultured with 50 mg of a liver tissue in a trans-well of a 6-well plate (BECTON DCKINSON) with a membrane (pore size, 0.4 µm) separating the cells from the tissue. The liver tissue was obtained from male C57BL/6 mice that had been exposed to a hepatotoxic reagent (e.g., thioacetamide, SIGMA-ALDRICH, St. Louis, Mo.) at 350 mg/kg, intraperitoneally 24 hours prior to the co-culture experiment. On day 2 and day 4 during the co-culture, total RNAs from WJSCs were extracted and cDNAs were prepared as a template for Polymerase Chain Reaction (PCR) analysis of liver-specific genes.

The PCR was carried out under the following conditions: 35 cycles total with each cycle consisting of denaturation for 30 sec at 95° C., annealing for 30 sec at 56-60° C. (based on the primer set used), and elongation for 60 sec at 72° C., with a final 10-min incubation at 72° C. The amplified DNAs using the primer pairs listed below were analyzed by gel electrophoresis.

Albumin:

(F) 5'-TGCTTGAATGTGCTGATGACAGGG-3' (SEQ ID NO: 1)
and
(R) 5'-AAGGCAAGTCAGCAGGCATCTCATC-3'. (SEQ ID NO: 2)

Tryptophan 2,3-dioxygenase:

(F) 5'-TGGTACTCTCCTCAATCTGCTG-3' (SEQ ID NO: 3)
and
(R) 5'-CTCTGGATTGACTGTGGAAGT-3'; (SEQ ID NO: 4)

α-Fetoprotein:

(F) 5'-ATACAGAGACTTCAGGAGC-3' (SEQ ID NO: 5)
and
(R) 5'-GTGAAGAGGGAAGACATAACTG-3'. (SEQ ID NO: 6)

Hepatocyte growth factor (HGF):

(F) 5'-CAGATCATCCATTGCATTCG-3' (SEQ ID NO: 7)
and
(R) 5'-ACTCCAGAGGCATTTCCATG-3'. (SEQ ID NO: 8)

Metalloproteinase (MMP):

(F) 5'-TgAATgCCCTTgATgTCATCCT-3' (SEQ ID NO: 9)
and
(R) 5'-ACACCTACACCAAgAACTTC-3'. (SEQ ID NO: 10)

CYP7A1:

(F) 5'-GAGAAGGCAAACGGGTGAAC-3' (SEQ ID NO: 11)
and
(R) 5'-ATCGGGTCAATGCTTCTGTG-3'. (SEQ ID NO: 12)

Nanog:

(F) 5'-TGCCTCACACGGAGACTGTC-3' (SEQ ID NO: 13)
and
(R) 5'-TGCTATTCTTCGGCCAGTTG-3'. (SEQ ID NO: 14)

OCT 4:

(F) 5'-CTTGCTGCAGAAGTGGGTGGAGGAA-3' (SEQ ID NO: 15)
and
(R) 5'-CTGCAGTGTGGGTTTCGGGCA-3'. (SEQ ID NO: 16)

ckit:

(F) 5'-ATGAGAGGCGCTCGCGGCGC-3' (SEQ ID NO: 17)
and
(R) 5'-AGCTTGGCAGGATCTCTAAC-3'. (SEQ ID NO: 18)

Glyceraldehyde 3 phosphate dehydrogenase:

(F) 5'-GGGCTGCTTTTAACTCTGGT-3' (SEQ ID NO: 19)
and
(R) 5'-GCAGGTTTTTCTAGACGG-3'. (SEQ ID NO: 20)

Establishment of a Rat Liver Fibrosis Model and Determination of Liver Fibrosis

Wistar Kyoto (WKY) rats were obtained from LASCO CO., LTD (Taipei, Taiwan). All procedures followed the ethical guidelines and were approved by the institutional Animal Care and Use Committee of Dong-Hwa University.

To establish the chronic liver fibrosis model in rat, 20 adult male WKY rats (320±20 g) were used. Twelve of them were intraperitoneally injected with 200 mg/kg thioacetamide (SIGMA-ALDRICH) once every 3 days for 60 days (i.e., 20 injections) as a fibrosis model group. The remaining 8 rats were injected with normal saline in place of the thioacetamide as a normal control group. At day 64 (i.e., 4 days after the last injection), these rats were sacrificed. Cardiac blood samples and liver samples were collected.

The blood samples were analyzed using a biochemical analyzer (INTEGRA 800; ROCHE, Holliston, Mass., USA) to measure the liver function index, which included glutamate oxaloacetate transaminase (GOT), glutamate pyruvate transaminase (GPT), serum albumin and prothrombin time.

Meanwhile, liver tissue samples were analyzed for their histopathology, i.e., fibrosis, caused by an excessive accumulation of collagen in liver using Masson's trichrome staining, as described by Bataller et al., 2005, J. Clin. Invest. 115(2): 209-218. Briefly, liver tissue samples were fixed in 3.7% formaldehyde and then embedded in paraffin. Serial 3-μm sections of the embedded tissues were stained with hematoxylin and eosin or Masson's trichrome.

For Masson's trichrome staining, sectioned samples were placed in Bouin's solution (SIGMA-ALDRICH) at 56° C. for 1 hour and then were incubated sequentially with the following solutions: Mayer's hematoxylin solution (SIGMA-ALDRICH) for 5 minutes, Biebrich scarlet-acid fuchsin solution (SIGMA-ALDRICH) for 15 minutes, phosphomolybdic acid-phosphotungstic acid (SIGMA-ALDRICH) for 15 minutes, and aniline blue (SIGMA-ALDRICH) for 5 minutes.

The liver fibrosis in each experimental group was quantified using the method described in Bruck et al., 2007, J. Gastroenterol. Hepatol. 22(12):2189-2194. Briefly, the Masson's trichrome stained liver tissue slices were photographed and scored semiquantatively at a scale of 0 to 3 by three independent pathologists. The degree of the liver fibrosis was determined by averaging scores in 10 different fields within each slide. The higher the score is, the more serious the liver fibrosis is.

Cell Transplantation Procedure

WJSCs ($2 \times 10^7$) that had been cultured with a thioacetamide-injured liver tissue in 75-cm$^2$ T-flasks as described above were detached by trypsinization and collected by centrifugation. These cells were then resuspended in normal saline at a concentration of $2\times10^6$ cells/ml.

Cell transplantation was carried out according to a protocol modified from those described in Abdel Aziz (Abdel Aziz et al., 2007, Clin. Biochem. 40(12):893-899 and Zhao et al., 2005, World J. Gastroenterol. 11(22):3431-3440). In cell transplantation experiment, 30 rats with thioacetamide-induced fibrotic livers were used for cell transplantations at day 64 (i.e., 4 days after the last thioacetamide injection) as mentioned above in establishment of the rat liver fibrosis model. These rats were randomly divided into two groups: a WJSC group and a sham group. Fifteen rats in the WJSC group were anesthetized with ether and injected with $1\times10^6$ WJSCs (in 0.5 ml of normal saline) via the portal vein. The rats in the sham group were injected with 0.5 ml normal saline only.

After transplantation, five rats each from the WJSC and sham groups were sacrificed weekly for 3 weeks. The biochemical liver function index and liver histopathology were analyzed at each time point as described in the previous section.

Characterization of Transplanted WJSCs

Monoclonal antibodies specific for human albumin, human mitochondria, metalloproteinase and human hepatocyte growth factor were used to determine whether the transplanted WJSCs would express hepatic markers as described above. Briefly, sectioned paraffin-embedded liver samples were subjected to immunohistochemical analysis using anti-human albumin (1:1000; SIGMA-ALDRICH), anti-metalloproteinase (1:200; ABCAM, Cambridge, Mass., USA) and anti-human hepatocyte growth factor (1:200, ABNOVUS, Walnut, USA). Subsequently, an immunohistochemistry kit (INNOGENEX, San Ramon, Calif., USA) was used to visualize the antigens. To detect antigens using fluorescence microscopy, sectioned paraffin-embedded liver samples were incubated overnight with anti-human mitochondria (1:50; CHEMICON, Billerica, Mass., USA) and subsequently incubated with rhodamine-conjugated anti-mouse secondary antibody (CHEMICON, Billerica, Mass., USA).

Statistical Analysis

All data were shown as a mean with a standard deviation. For the comparison between data from treated and control groups, Student's t-test was used. To be considered statistically different between groups, p values should be less than 0.05.

Results

Characterization of WJSCs

WJSC morphology and surface markers were determined by microscopy and flow cytometry, respectively. The surface markers of WJSCs were similar to that described previously for WJSCs (Tang et al., 2006, World J. Gastroenterol. 12(25): 4014-4019). The WJSCs obtained in this study did not have hematopoietic markers CD 14, CD34, CD45, or the major histocompatibility complex marker HLA-DR, but carried the mesenchymal stem cell markers (i.e., CD29, CD44, CD49b, CD49d, CD73, CD90, and CD105), and a myeloid marker (i.e., CD13), as shown in FIG. 1A-M. In addition, these cells showed a fibroblast-like morphology as shown in FIG. 1N.

Figure 2:
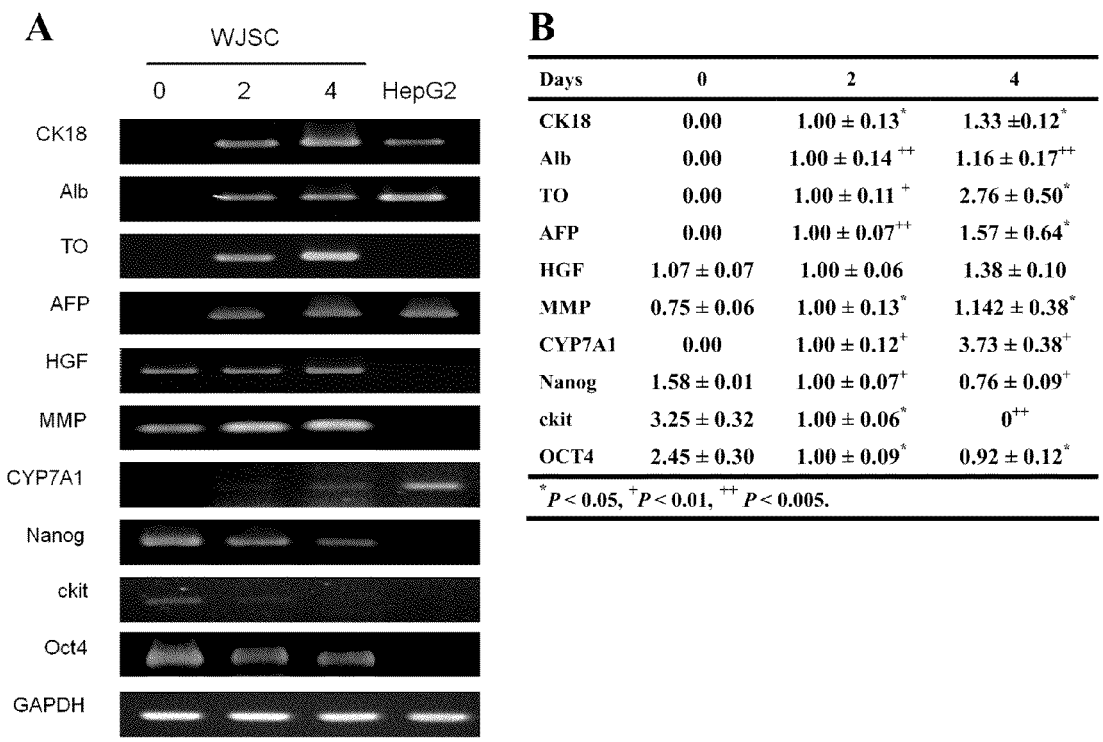
FIGS. 2A and 2B are photographs of RT-PCR and gel electrophoresis of expression of hepatic-specific genes (A) and a table of semi-quantitative RT-PCR result (B) showing the expression of liver-specific genes in WJSC as a measure of their hepatic differentiation at Day 0, 2, or 4 after co-culturing with thioacetamide-injured liver tissue.

To show whether WJSCs were able to undergo hepatic differentiation by co-culturing with TAA-damaged mouse liver tissue, hepatic markers were determined using the method described above. RT-PCR showed that WJSCs cultured under the differentiating conditions gained expression of liver-specific genes, including CK18, albumin, TO, AFP, and CYP7A1 (FIG. 2). In addition, the gene expression of HGF and MMP were increased. At the same time, the expression of stem cell genes, including nanog, oct4 and ckit, in the differentiated WJSCs were decreased. These results suggest that the WJSCs have a potential to differentiate into hepatocyte-like cells in vitro.

Characterization of a Liver Fibrosis Model and Evaluation of WJSC Cell Therapy

As shown in Table 1 below, in liver fibrosis rat group, the GOT and GPT levels, compared to normal rat group, were significantly increased (GOT from 110±16 U/L to 1034±361 U/L, and GPT from 77±10 U/L to 185±50 U/L), indicating liver damage.

TABLE 1

Plasma biochemical value of normal rats and liver fibrosis rats

|  | Normal rats (n = 8) | Liver fibrosis rats (n = 12) |
|---|---|---|
| GOT (U/L) | 110 ± 16 | 1034 ± 361** |
| GPT (U/L) | 77 ± 10 | 185 ± 50* |
| Albumin (g/dL) | 4.11 ± 0.11 | 3.43 ± 0.08** |
| Prothrombin time (sec) | 9.4 ± 0.11 | 11.5 ± 1.0** |

Note:
Data represent mean ± standard deviation.
*P < 0.05,
**P < 0.01, the liver fibrosis rats compared to the normal rats.

Significantly decreased albumin levels (from 4.11±0.43 g/dL to 3.43±0.08 g/dL) and significantly increased prothrombin time (from 9.4±0.11 sec to 11.5±1.0 sec) were also found in the blood. The biochemical results in the thioacetamide-induced liver fibrosis experiments were consistent with previous reports (Abdel Aziz et al., 2007, Clin. Biochem. 40(12):893-899), suggesting significantly reduced liver function in these animals.

In the WJSC group and the sham group, biochemical liver function indices were also examined (Table 2). GOT and GPT levels declined to near-normal values in both the WJSC and sham groups at day 7 after transplantation. GOT and GPT levels did not differ significantly between groups. The observed low GOT and GPT levels may be attributable to the short half-lives of GOT and GPT (i.e., 17 and 47 h, respectively) (Knapen et al., 1998, Am. J. Obstet. Gynecol. 178(1 Pt 1):161-165).

Although the GOT and GPT levels did not differ between groups, prothrombin time indicated significant differences between the two groups at 21 days and the albumin level was approaching normal level in WJSC group at 21 days. Prothrombin time was significantly different between the WJSC group and the sham group 21 days after transplantation (9.5±0.1 vs. 9.9±0.2, P<0.01). At 21 days post-transplantation, serum albumin in the WJSC group had recovered to a greater extent than in the sham group (3.84±0.22 vs. 3.52±0.14). These changes suggest that liver function had recovered after 21 days of WJSC therapy (Table 2).

TABLE 2

Effects of WJSC-transplantation on plasma biochemical values

|  | WJSC Day 7 (n = 5) | Sham Day 7 (n = 5) | WJSC Day 14 (n = 5) | Sham Day 14 (n = 5) | WJSC Day 21 (n = 5) | Sham Day 21 (n = 5) |
| --- | --- | --- | --- | --- | --- | --- |
| GOT (U/L) | 161 ± 30 | 127 ± 35 | 131 ± 29 | 136 ± 26 | 151 ± 36 | 136 ± 17 |
| GPT (U/L) | 82 ± 23 | 84 ± 5 | 86 ± 8 | 78 ± 17 | 89 ± 18 | 95 ± 10 |
| Albumin (g/dL) | 3.79 ± 0.04 | 3.73 ± 0.04 | 3.79 ± 0.08 | 3.79 ± 0.16 | 3.84 ± 0.22 | 3.52 ± 0.14 |
| Prothrombin time (sec) | 9.9 ± 0.3 | 10.0 ± 0.3 | 9.9 ± 0.2 | 10.0 ± 0.2 | 9.5 ± 0.1** | 9.9 ± 0.2 |

Data represent mean ± standard deviation.
WJSC: TAA-induced liver fibrosis rats transplanted with WJSC
Sham group: TAA-induced liver fibrosis rats treated with 0.5 ml normal saline
**$P < 0.01$, WJSC at 21 days compared to the sham at day 21.

Figure 3:
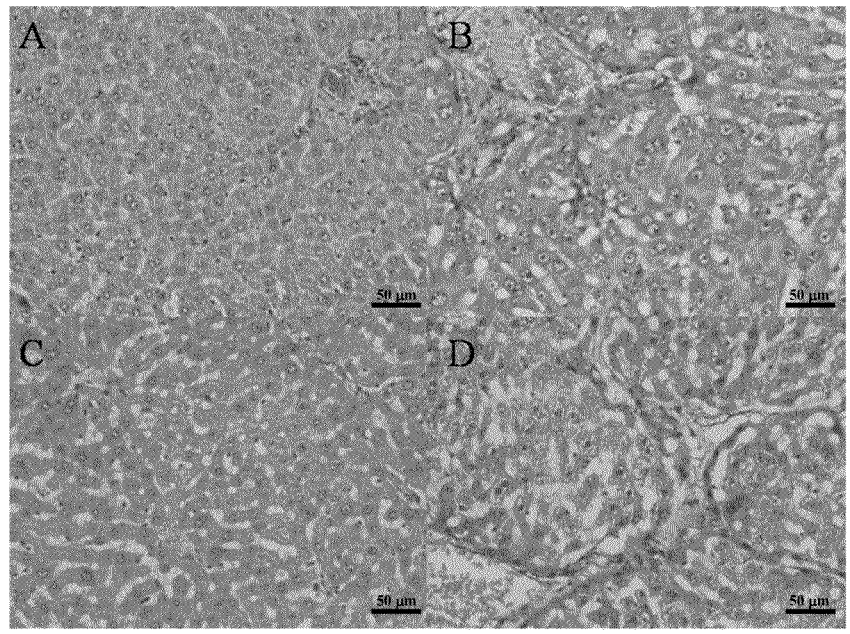
FIGS. 3A-D are photographs of hematoxylin and eosin staining of rat liver sections a normal rat (A), (B) liver section of a liver fibrosis rat injected with TAA 200 mg/kg once every 3 days for 60 days (B), liver section of WJSC group at day 21 after WJSC transplantation (C), and liver section of sham group at day 21 after normal saline injection (D). Bar=50 μm.

Hematoxylin and eosin staining of normal rat liver tissue sections indicated that there was no damage, as expected (FIG. 3A). In comparison, tissue vacuolation, necrosis and the degeneration of cell nuclei were observed in liver sections from thioacetamide-induced liver fibrosis rats (FIG. 3B). Histopathologic data suggested that WJSC transplantation ameliorated liver damage. The recovery of tissue degeneration and vacuolation was evident in the WJSC group at day 21, whereas the sham group still showed serious inflammation and necrosis (FIGS. 3C and D, respectively).

Figure 4:
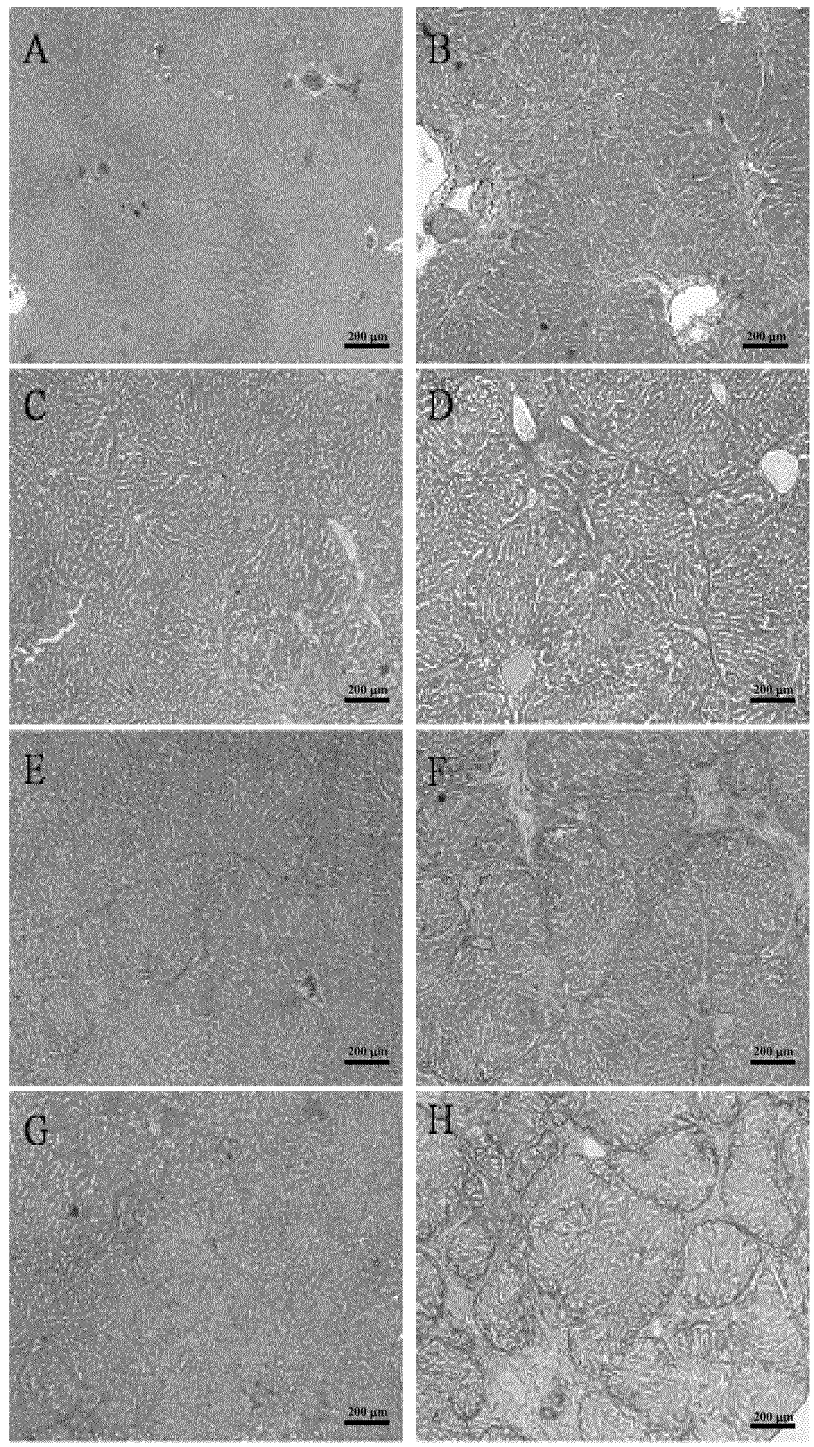
FIGS. 4A-H are photographs of Masson's trichrome staining of liver sections of a normal rat (A), liver fibrosis rat (B), liver section of WJSC group at day 7 (C), liver section of WJSC group at day 14 (E), liver section of WJSC group at day 21 (G), liver section of sham group at day 7 (D), liver section of sham group at day 14 (F), and liver section of sham group at day 21 (H). Bar=200 μm.

Masson's trichrome stain revealed severe accumulation of collagen in livers from the liver fibrosis rat group (FIG. 4). The quantification of liver fibrosis degree in liver fibrosis rat group was significant higher than normal rat group (Table 3).

TABLE 3

The quantity score of liver fibrosis in each experimental group.

| Treatment | Fibrosis score (0-3) |
| --- | --- |
| Normal rats (n = 8) | 0 |
| Liver fibrosis rats (n = 12) | 2.36 ± 0.49 |
| Sham day 7 (n = 5) | 2.27 ± 0.45 |
| WJSC day 7 (n = 5) | 2.03 ± 0.49 |
| Sham day 14 (n = 5) | 2.2 ± 0.48 |
| WJSC day 14 (n = 5) | 1.47 ± 0.57** |
| Sham day 21 (n = 5) | 2.23 ± 0.43 |
| WJSC day 21 (n = 5) | 0.87 ± 0.34** |

Values shown as mean ± SD.
Normal rats: Rats did not receive any treatment.
Liver fibrosis rats: Rats were injected with TAA 200 mg/kg once every 3 days for 60 days.
Sham group: TAA-induced liver fibrosis rats were injected with 0.5 ml saline via portal vein.
WJSC group: TAA-induced liver fibrosis rats were transplanted with WJSCs via portal vein.
**$P < 0.01$, the WJSC at day 14 compared to the Sham at day 14 and the WJSC at day 21 compared to the sham at day 21.

The above results suggested that TAA injection indeed induced liver fibrosis in rats. "Bridging", which results from accumulated collagen that connects two blood vessels, was found in most areas in liver fibrosis group (FIG. 4B). This phenomenon was very similar to previous liver fibrosis reports (Anand et al., 1999, West. J. Med. 171(2):110-115; Bataller et al., 2005, J. Clin. Invest. 115(2):209-218; Kershenobich et al., 2003, Ann. Hepatol. 2(4):159-163 and Lee, 2006, Korean J. Gastroenterol. 48(5):297-305) and was not found in the control group (FIG. 4A).

Masson's trichrome staining was used to assess collagen expression. It was found that no difference in collagen contents at day 7 in the ten rats analyzed from each group (FIG. 4C, D and Table 3). Collagen degradation was found at day 14 in the WJSC group (FIG. 4E, F and Table 3). The WJSC group rarely showed collagen accumulation at day 21 (FIG. 4G and Table3), whereas the sham group still showed substantial collagen accumulation (FIG. 4H and Table 3) day 21 after transplantation.

Detection of Hepatic Markers in Transplanted WJSCs

Figure 5:
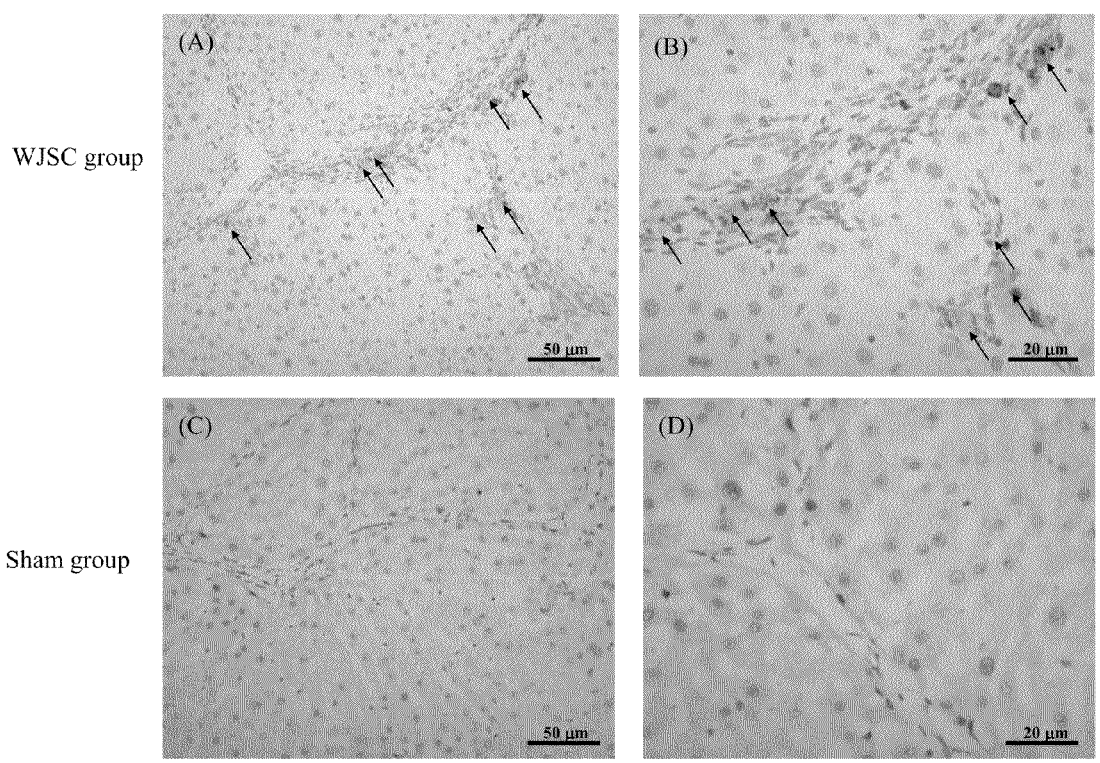
FIGS. 5A-D are photographs of human albumin immunostaining of liver sections from WJSC group (A and B) and sham group (C and D) at day 21 after transplantation. (A and D) Bar=50 μm. (B and E) Bar=20 μm.

To follow the transplanted human cells in this study, antibodies specific for human albumin, human mitochondria, metalloproteinase and human HGF were used to stain sectioned liver samples. The human albumin positive cells was detected in the WJSC group up to 21 days after transplantation (FIGS. 5A and B) but in sham group the albumin-positive cells were not detected (FIGS. 5C and D). This result suggested that the transplanted WJSCs differentiated into albumin-secreting hepatocyte-like cells in the damaged livers of the rats from the WJSC group. Immunohistochemical staining for metalloproteinase revealed many metalloproteinase-positive cells in the peri-venule and bile duct areas in the WJSC group (FIG. 6A). However, metalloproteinase-positive and human mitochondria-positive cells were not observed in the sham group (FIGS. 6B and D). The metalloproteinase-positive cells in the WJSC group were also co-stained with human mitochondria (FIG. 6C) but it is not observed in the sham group. This indicated that these metalloproteinase-positive cells were transplanted WJSCs. Further, the human HGF-positive cells were observed and along the collagen fiber in damaged liver of WJSC group (FIG. 7A) but it is not observed in the sham group. This indicated the transplanted WJSCs could express human HGF in damaged liver.

Discussion

We have established a model system for studying liver damage following periodic injections of thioacetamide. In this study, WJSCs had the potential to differentiate into hepatocyte-like cells when co-cultured with chemically-damaged liver in vitro. The biochemical liver function index and histopathological analysis from in vivo experiments revealed that the human WJSCs promoted the recovery of thioacetamide-induced hepatic damage and thus can be used in cell therapy.

Figure 7:
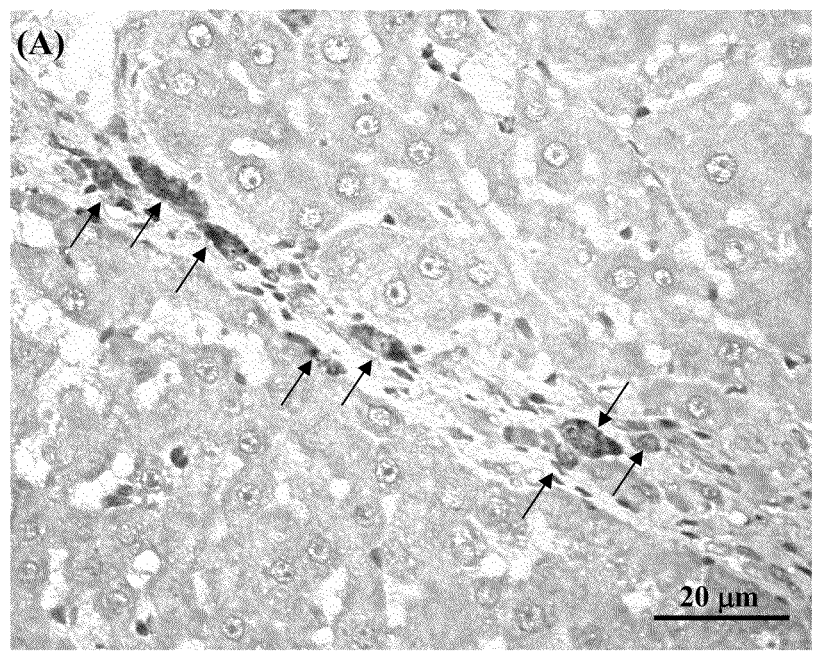
FIGS. 7A and B are photographs of human HGF immunostaining of liver sections from the WJSC group (A) and the sham group treated by normal saline (B) at day 21 after transplantation. Bar=20 μm.
Figure 7:
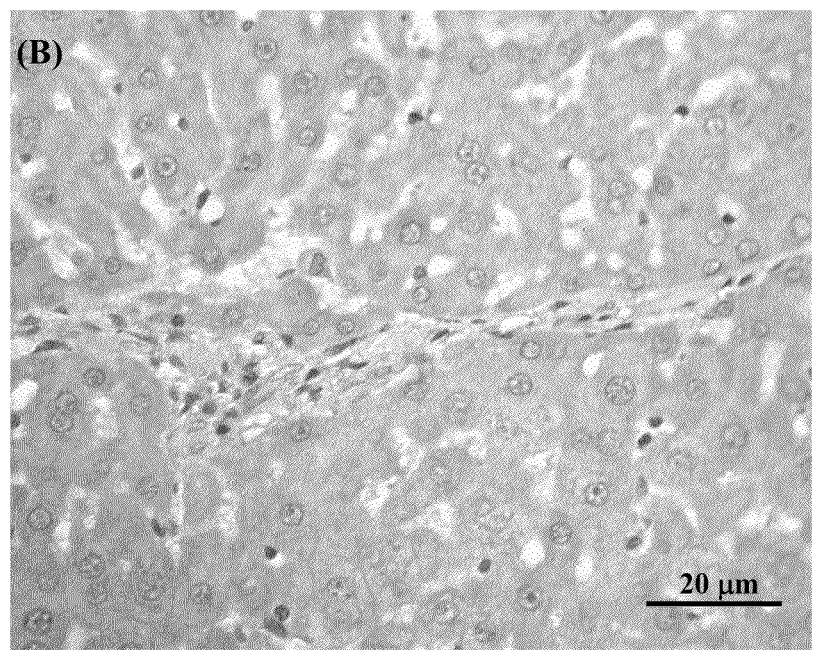

There are several explanations for the amelioration of thioacetamide-induced liver damage facilitated by WJSCs. First, immunostaining of WJSCs incorporated into the thioacetamide-induced fibrotic liver indicated that WJSCs could differentiate into albumin-producing hepatocyte-like cells (FIGS. 5A and B). The in vitro study showed that WJSCs expressed liver-specific genes when co-cultured with the chemically damaged liver tissue (FIG. 2). These hepatocyte-like cells that differentiated from Wyss may play an important role in the recovery of liver function. Moreover, in the animal study, the WJSCs-derived hepatocyte-like cells were likely responsible for facilitating the recovery of thioacetamide-induced cell damage. Second, HGF might play a role in the acceleration of the recovery. HGF can facilitate regeneration of the damaged liver because of its anti-apoptotic effects of its signaling through c-met. The WJSCs used in this study could express HGF mRNA (FIG. 2) and secrete HGF at the site of a fibrotic liver (FIG. 7). This suggests that HGF secreted by the WJSCs accelerates liver recovery. Third, the collagen content in the WJSC group decreased week by week; at day 21 post-transplantation, there was little collagen in liver sections. By comparison, the sham-treated group showed no collagen decrease (FIG. 4 and Table 1). The above study is the first to describe such a reduction in collagen deposition in response to WJSC treatment.

Figure 6:
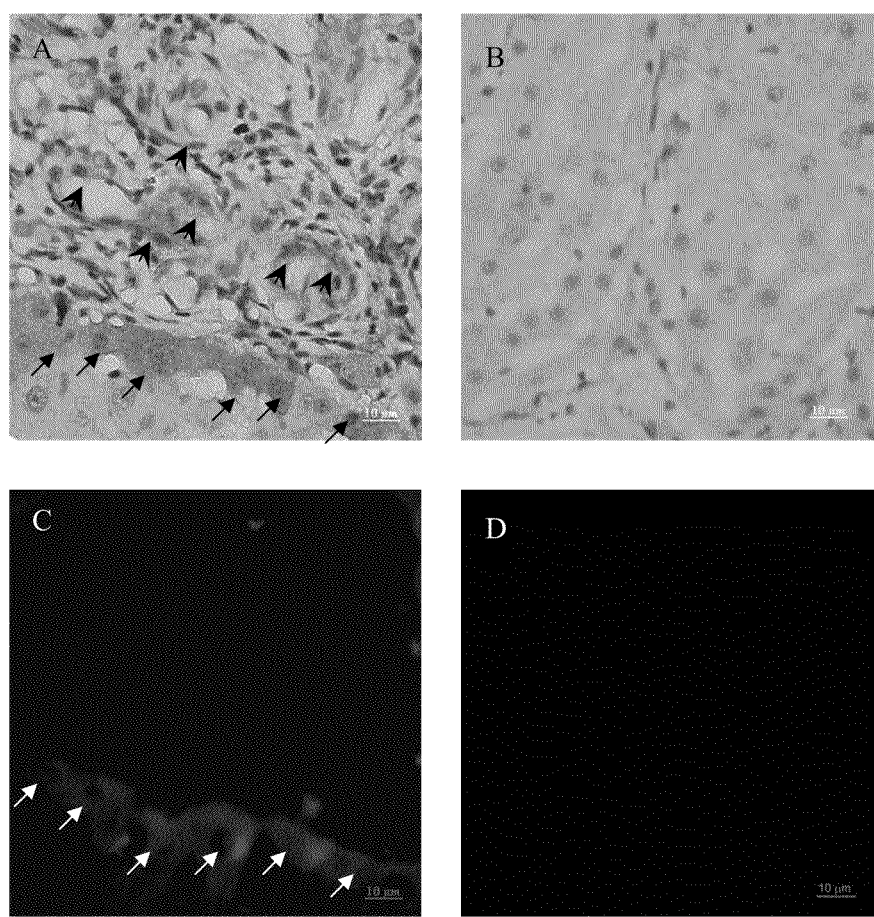
FIGS. 6A-D are photographs of immunostaining for human metalloproteinase and mitochondria in liver sections of WJSC group and sham group at day 21 after transplantation. (A) The immunostaining for metalloproteinase in liver sections from a WJSC rat. (B) The immunostaining for metalloproteinase in liver sections from a sham rat. (C) The immunostaining for human mitochondria in liver sections from a WJSC rat. (D) The immunostaining for human mitochondria in liver sections from a sham rat. Black and white Arrows: metalloprotease and human mitochondria-positive cells. Arrowheads: metalloprotease-positive bile duct cells. Bar=10 μm.

The matrix metalloproteinase family plays an important role in collagen degradation (Gordon et al., 2006, Stem Cells 24(7):1822-1830 and Iimuro et al., 2008, Pharm. Res. 25(2): 249-258). As shown in FIG. 6, metalloproteinase level significantly increased in WJSC-treated rats 21 days after WJSC transplantation. Increased metalloproteinase expression was observed in the peri-venule area in the study described herein, where Wyss were often observed. Interestingly, metalloproteinases were also present in the proliferating bile ducts where no WJSC were observed. One possible explanation is that WJSCs generated a microenvironment that induced metalloproteinase expression in bile ducts. Both sources of induced metalloproteinase expression may contribute to the degradation of collagen fibers in thioacetamide-induced liver fibrosis.

In conclusion, the above results demonstrate that WJSCs could different into hepatocyte-like cells. The WJSC also could express MMP and HGF. In addition, in an in vivo study WJSCs differentiated into hepatocyte-like cells. Besides, WJSCs could express HGF and metalloproteinase, an attribute that also was observed in the surrounding bile duct, in vivo. The expression of HGF and metalloproteinase in undifferentiated WJSC as well as the WJSC-mediated differentiation of cells into hepatocyte-like cells facilitated the regeneration of a damaged liver with thioacetamide-induced liver fibrosis. WJSCs thus are a promising source of cells for treating liver fibrosis, cirrhosis, and other liver diseases.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising a preparation containing cultured pluripotent animal cells that are (i) positive for CD29, CD44, CD49b, CD49d, CD73, CD90, CD105, and CD 13; and (ii) negative for CD14, CD34, HLA-DR, and CD45; and a liver tissue.

2. The composition of claim 1, wherein the liver tissue is an isolated liver tissue.

3. The composition of claim 1, wherein the liver tissue is an injured liver tissue has been subjected to a hepatotoxic agent.

4. The composition of claim 1, wherein the pluripotent animal cells are obtained from the Wharton's jelly of the umbilical cord of a first subject.

5. The composition of claim 4, wherein the first subject is a human.

6. The composition of claim 4, wherein the liver tissue is obtained from a second subject.

7. A method for obtaining hepatic progenitor cells, comprising culturing the composition of claim 1 in a medium for a period of time; and collecting progenies of the cultured pluripotent animal cells to obtain hepatic progenitor cells, wherein the pluripotent animal cells are obtained from the Wharton's jelly of the umbilical cord of a first subject.

8. The method of claim 7, wherein the hepatic progenitor cells express one or more of genes selected from the group consisting of CK18, albumin, tryptophan 2,3-dioxygenase (TO), afetoprotein (AFP), CYP7A1, nanog, oct4, ckit, HGF, and MMP.

9. The method of claim 8, wherein the pluripotent animal cells are positive for HGF or MMP.

10. The method of claim 7, wherein the first subject is a human.

11. The method of claim 7, wherein the liver tissue is an injured liver tissue.

* * * * *

SEQUENCE LISTING

```
<160> NUMBER OF SEQ ID NOS: 20

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
tgcttgaatg tgctgatgac aggg                                        24

<210> SEQ ID NO 2
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 2
aaggcaagtc agcaggcatc tcatc                                       25

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 3
tggtactctc ctcaatctgc tg                                          22

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide
```

```
<400> SEQUENCE: 4
ctctggattg actgtggaag t                                              21

<210> SEQ ID NO 5
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 5
atacagagac ttcaggagc                                                 19

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
gtgaagaggg aagacataac tg                                             22

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
cagatcatcc attgcattcg                                                20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
actccagagg catttccatg                                                20

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 9
tgaatgccct tgatgtcatc ct                                             22

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
acacctacac caagaacttc                                                20

<210> SEQ ID NO 11
<211> LENGTH: 20
<212> TYPE: DNA
```

-continued

<213> ORGANISM: Artificial sequence
<220> FEATURE:
<223> OTHER INFORMATION: Synthetic oligonucleotide

<400> SEQUENCE: 11
gagaaggcaa acgggtgaac                                                    20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
atcgggtcaa tgcttctgtg                                                    20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tgcctcacac ggagactgtc                                                    20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
tgctattctt cggccagttg                                                    20

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 15
cttgctgcag aagtgggtgg aggaa                                              25

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 16
ctgcagtgtg ggtttcgggc a                                                  21

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
atgagaggcg ctcgcggcgc                                                    20

```
<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
agcttggcag gatctctaac                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
gggctgcttt taactctggt                                              20

<210> SEQ ID NO 20
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 20
gcaggttttt ctagacgg                                                18
```